(12) United States Patent
Roszkowiak (10) Patent No.: US 11,969,326 B2
(45) Date of Patent: Apr. 30, 2024

(54) MULTILAYER BLADDER CONTROL PAD

(71) Applicant: Medline Industries, Inc., Northfield, IL (US)

(72) Inventor: Amanda Roszkowiak, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 1066 days.

(21) Appl. No.: 16/740,125

(22) Filed: Jan. 10, 2020

(65) Prior Publication Data

US 2020/0222253 A1    Jul. 16, 2020

Related U.S. Application Data

(60) Provisional application No. 62/792,534, filed on Jan. 15, 2019.

(51) Int. Cl.
*A61F 13/53* (2006.01)
*A61F 13/47* (2006.01)
(Continued)

(52) U.S. Cl.
CPC ............. *A61F 13/53* (2013.01); *A61F 13/47* (2013.01); *A61F 13/51478* (2013.01);
(Continued)

(58) Field of Classification Search
CPC .............. A61F 13/53; A61F 13/47; A61F 2013/530481; A61F 2013/53089; A61F 2013/53908; A61F 2013/53445; A61F 13/534; A61F 13/539; A61F 13/55145; A61F 13/505; A61F 13/4756;
(Continued)

(56) References Cited

U.S. PATENT DOCUMENTS

| 4,505,707 A | 3/1985 | Feeney |
| 4,576,597 A * | 3/1986 | Hlaban ............... A61F 13/5611 604/389 |

(Continued)

FOREIGN PATENT DOCUMENTS

| WO | 1998017220 A1 | 4/1998 |
| WO | 2015094029 A1 | 6/2015 |
| WO | 2016053725 A1 | 4/2016 |

OTHER PUBLICATIONS

United States Statutory Invention Registration; Registration No. H1788, Christon et al.Published Feb. 2, 1999.

(Continued)

*Primary Examiner* — Susan S Su
(74) *Attorney, Agent, or Firm* — Gurr Brande & Spendlove, PLLC; Robert D. Spendlove (57) ABSTRACT

The absorbent pad has a first layer, a second layer, and a third layer. Each layer of the pad has a liquid impervious back sheet. The backsheet or outer layer, which faces away from the wearer when the absorbent article is secured to the wearer, is composed of a moisture-impervious, flexible material. Further, each layer has a moisture pervious inner layer and an absorbent core positioned in between the inner layer and back sheet. The layers are coupled to each other via an adhesive. They can be removed by grasping a tab placed on each layer and pulling the layer away from the unsoiled layers.

20 Claims, 9 Drawing Sheets

(51) Int. Cl.
*A61F 13/514* (2006.01)
*A61F 13/539* (2006.01)

(52) U.S. Cl.
CPC .............. *A61F 2013/530481* (2013.01); *A61F 2013/53089* (2013.01); *A61F 2013/53908* (2013.01)

(58) Field of Classification Search
CPC .......... A61F 13/55105; A61F 13/55115; A61F 13/5516; A61F 13/55165
See application file for complete search history.

(56) References Cited

U.S. PATENT DOCUMENTS

| | | | |
|---|---|---|---|
| 5,405,342 A | 4/1995 | Roessler et al. | |
| 5,429,631 A | 7/1995 | Grenier | |
| 5,599,339 A * | 2/1997 | Horney | A61F 13/474 604/389 |
| 5,704,932 A * | 1/1998 | Hibbard | A61F 13/505 604/386 |
| 5,820,616 A * | 10/1998 | Horney | A61F 13/474 604/385.04 |
| 5,910,137 A | 6/1999 | Clark et al. | |
| 6,280,427 B1 * | 8/2001 | Maggiulli | A61F 13/474 604/386 |
| 6,730,067 B1 * | 5/2004 | Nukina | A61F 13/474 604/385.01 |
| 10,159,609 B2 | 12/2018 | Kleuskens et al. | |
| D961,068 S * | 8/2022 | Manzione | D24/124 |
| 2001/0027304 A1 * | 10/2001 | Mayer | A61F 13/474 604/385.04 |
| 2006/0247590 A1 * | 11/2006 | Ito | A61F 13/474 604/378 |
| 2011/0319854 A1 * | 12/2011 | Suga | A61F 13/51394 604/385.14 |
| 2012/0310202 A1 | 12/2012 | Wilson | |
| 2015/0005729 A1 * | 1/2015 | Nakao | A61F 13/15658 604/374 |
| 2016/0296385 A1 * | 10/2016 | Samuelsson | A61F 13/505 |
| 2016/0302978 A1 | 10/2016 | Lindstrom | |

OTHER PUBLICATIONS

International Search Report; International Patent Application No. PCT/US2020/013442; Medline Industries, Inc.; dated Apr. 23, 2020.
Written Opinion of the International Searching Authority; International Patent Application No. PCT/US2020/013442; Medline Industries, Inc.; dated Apr. 23, 2020.

* cited by examiner

MULTILAYER BLADDER CONTROL PAD

CROSS-REFERENCE TO RELATED APPLICATIONS

This application claims the benefit of U.S. Provisional Application Ser. No. 62/792,534, filed on Jan. 15, 2019, which is incorporated herein by reference.

FIELD OF THE INVENTION

The present invention relates generally to absorbent articles and, in particular, to the use of multiple absorbent layers in the article. Embodiments of the present invention relate primarily to absorbent articles such as disposable incontinence articles, namely, absorbent pads for placement in the undergarment of a user.

BACKGROUND OF THE INVENTION

Disposable absorbent articles are known in the prior art and have many uses.

Whether intended for infants, children, adults or the elderly, disposable pads, napkins, diapers, training pants, briefs, underwear, incontinence articles, hygienic articles and the like are intended to absorb and retain voids, exudate or other body discharges. As used herein, "absorbent article" will refer to these or other examples.

Active adults appreciate the freedom afforded to them by incontinence absorbent articles. Such disposable articles can alleviate some of the emotional and physical discomfort of incontinence by absorbing and containing body discharges. Problems arise, however, when there is a need to carry multiple articles for use over an extended period of time. Multiple such articles can be bulky and require space or be carried in ways that are inconvenient or embarrassing.

While there are variations in the specific structural features of disposable absorbent articles, they are frequently presented to the consumer in the same manner. Essentially, the disposable absorbent article, irrespective of specific structural features, is packaged in a box, bag or carton with a plurality of disposable absorbent articles from which the consumer withdraws the ready-to-use article as needed. When traveling or attending to the activities of daily life, bulk packages as described above are indiscreet and impractical.

Given these and other shortcomings of existing absorbent articles, embodiments of the present invention include an absorbent article, which may particularly include an incontinence pad, that allows the use of a single pad to be used multiple times. Advantages of this embodiment include extending the duration for which the pad may be used and reducing the number and bulk of pads that an individual may need to carry.

BRIEF DESCRIPTION OF THE DRAWINGS

The various aspects, features and advantages of the disclosure will become more fully apparent to those having ordinary skill in the art upon careful consideration of the following Detailed Description thereof with the accompanying drawings described below.

While embodiments of the invention are susceptible to various modifications and alternative forms, specific embodiments have been shown by way of example in the drawings and will be described in detail herein. It should be understood however, that the invention is not intended to be limited to the particular forms disclosed. Rather, the invention will cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly indicates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Integral" is used to refer to various portions of a single unitary element rather than separate structures bonded to or placed with or placed near one another.

"Extensible" refers to materials which elongate or increase in at least one dimension when subject to an external pulling force.

"Elastomeric" refers to a material or composite which can be elongated by a percent of its relaxed length and which will recover, upon release of the applied force by a percent of its elongation. In certain embodiments, an elastomeric material or composite may be capable of being elongated by at least 100 percent, in further embodiments by at least 300 percent of its relaxed length. Embodiments of the elastic material or composite may recover, upon release of an applied force, at least 50 percent of its elongation.

These terms may be defined with additional language elsewhere in the specification.

Although the remainder of the description will be specifically directed to adult incontinence articles, including specifically, absorbent pads for placement in a user's undergarment (whether intended for men or women) to absorb bladder leakage, it is understood that the embodiments may also be implemented on other absorbent articles, whether intended for infants, children, adults or the elderly. As would be understood by one of ordinary skill in the art, such non-limiting examples include: disposable pads, napkins, diapers, training pants, and the like which are intended to absorb and retain body discharges.

Figure 1:
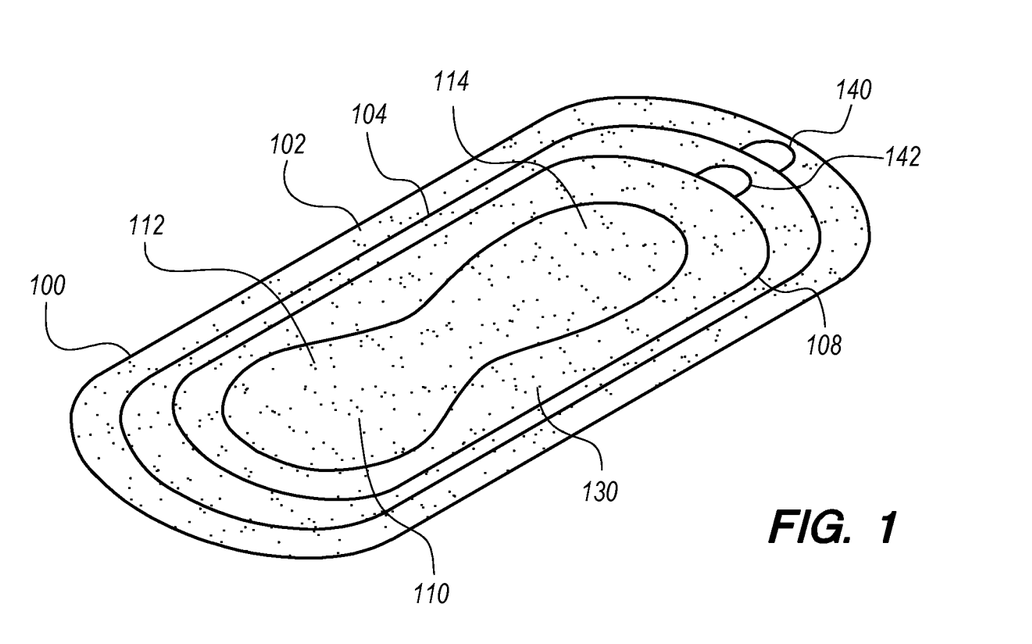
FIG. 1 is a perspective view of an embodiment of an absorbent pad having a plurality of individual, removeable cores.

Referring first to FIG. 1, embodiments of the absorbent pad 100 comprise a first layer 102, a second layer 104, and a third layer 106. Embodiments of the pad will be described herein having three layers. However, it should be understood that the pad may have more or fewer layers.

Each layer of the pad comprises a liquid impervious back sheet 108. The backsheet or outer layer, which faces away from the wearer when the absorbent article is secured to the wearer, is composed of a moisture-impervious, flexible material. Accordingly, backsheet 108 may be made of any material suitable to minimize or prevent fluids and other discharge from escaping the pad. Non-limiting examples of suitable materials for the backsheet include polyethylene and/or breathable poly. According to some embodiments, the outer layer can be a thin film such as, for example, polyethylene film. The outer layer may be formed from a plastic resin of any of the above-referenced materials.

In addition, each layer comprises an absorbent core 110. The absorbent core is positioned adjacent the backsheet proximal the wearer. The absorbent core may comprise a single layer or multiple layers. Embodiments of the absorbent core may comprise super absorbent fiber ("SAF"). Alternatively, the absorbent core may comprise super absorbent polymer ("SAP") or a combination of SAF and SAP. Embodiments of the absorbent core 110 may further comprise other materials suitable for absorbing the fluids and discharge such as a fibrous material (e.g., fluffed wood pulp). The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the core may vary depending upon whether it is intended for use by infants, children and/or adults. The absorbent core for each layer 102, 104, 106, may vary from layer to layer. For example, the first layer absorbent core may be a thinner SAP, while the second absorbent core may be thicker and SAF.

Embodiments of the core may include an embossed top and/or an embossed bottom. In this manner, the core 110 provides increased longitudinal movement of fluid on both the embossed top and embossed bottom of the core 110, and reduced lateral flow, decreasing the potential for leaks from the side of the absorbent article 100.

Each layer may further comprise an inner layer. The inner layer faces a wearer and contacts the skin of the wearer when the absorbent pad 100 is secured to the wearer. The inner layer may comprise a topsheet 130 that is composed of a moisture pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon-based chemicals.

Figure 2:
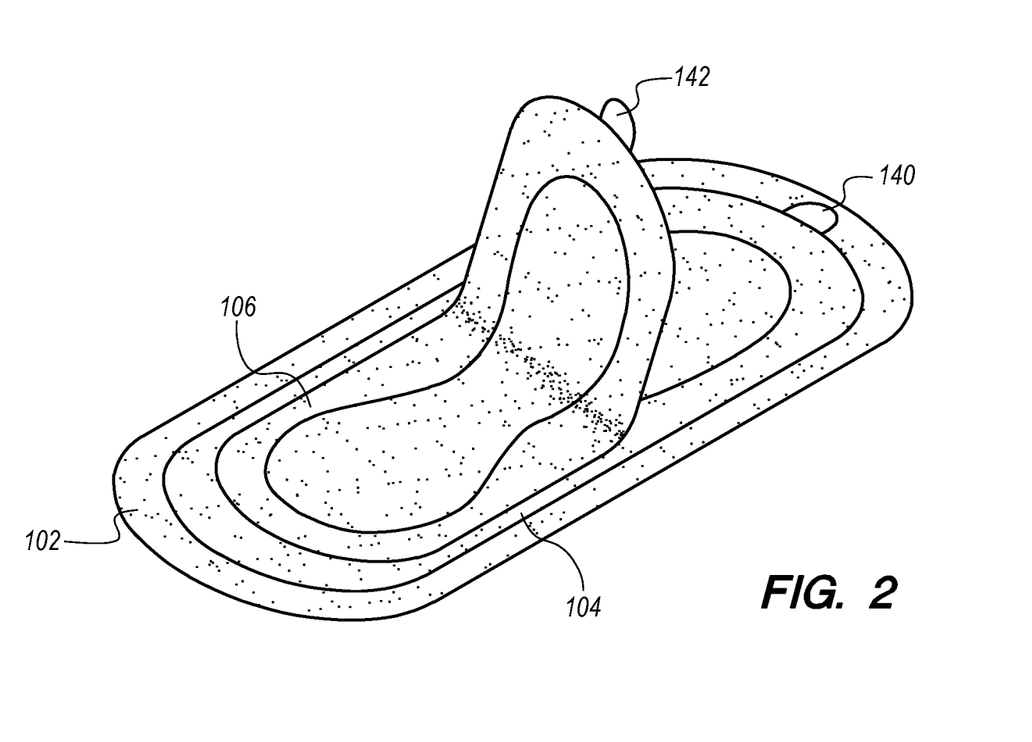
FIG. 2 is a perspective view of the embodiment of FIG. 1 as one of the cores being removed.

In embodiments of the absorbent pad, tabs 140, 142 may extend from, and be coupled to, an edge of the inner layers 104, 106. The tabs 140, 142 may be made from the same material that is used for the backsheet, such as, for example, polyethylene and/or breathable poly. The tabs 140, 142 can also be a polyethylene film or any soft, pliable material. It will also be appreciated that the tabs may be of any adequate material known in the prior art. The tabs 140, 142 may be in similar locations, in line, as shown in FIG. 1. Alternatively, the tabs 140, 142 may be placed, as shown in FIG. 2, with tab 142 on the side of third layer 106 and tab 140 on second layer 104 at a distance away from tab 142 (not overlaying each other). This can help prevent the wearer from trying to remove the wrong layer. Additionally, the tabs 140, 142 may be color coded, such as red and green, to assist the wearer in removing the soiled layers. Not only can color and distance of the tabs 140, 142 vary, but the size and shape may also vary. As shown in FIGS. 1-2, the tabs 140, 142, have a generally square shape. However, the tabs 140, 142 may also be circular, triangular, or any other non-limiting example. The tabs may also be narrower or wider than depicted in FIGS. 1-2.

Figure 3:
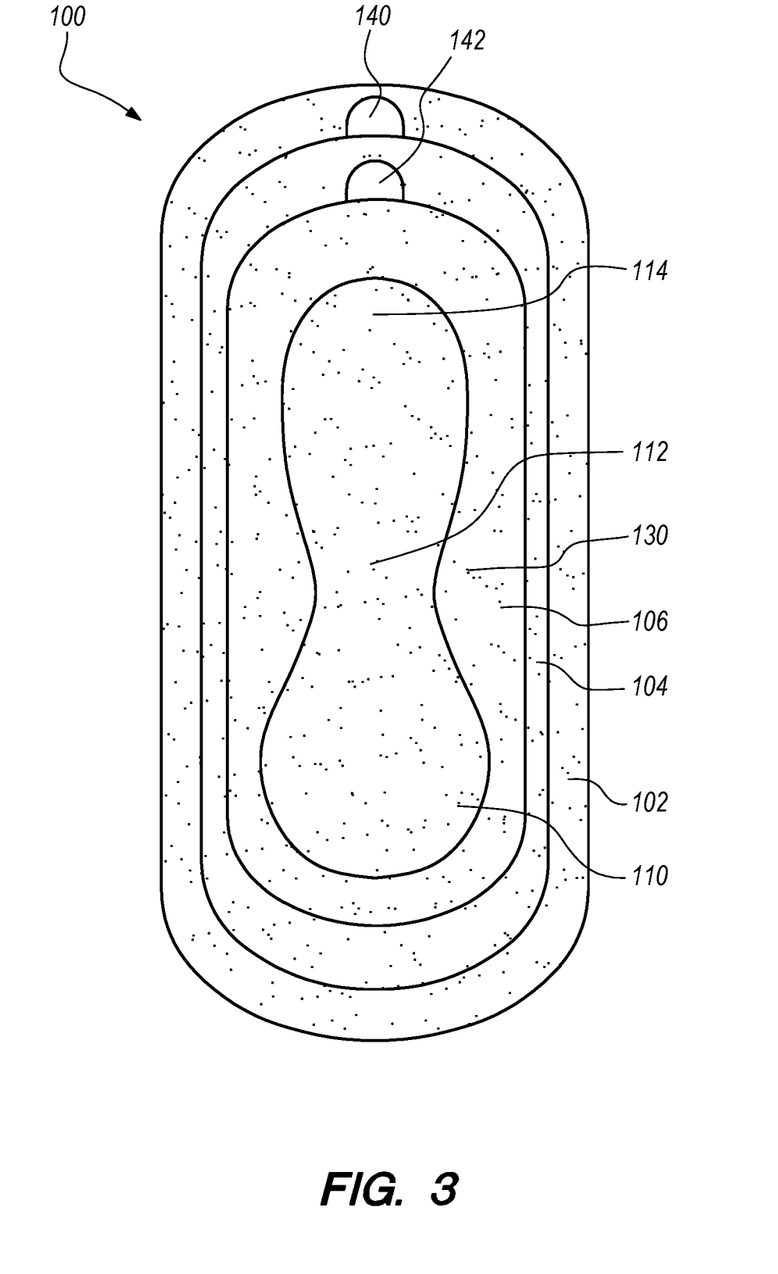
FIG. 3 is a top plan view of the embodiment of FIG. 1 having a plurality of individual, removeable cores.
Figure 4:
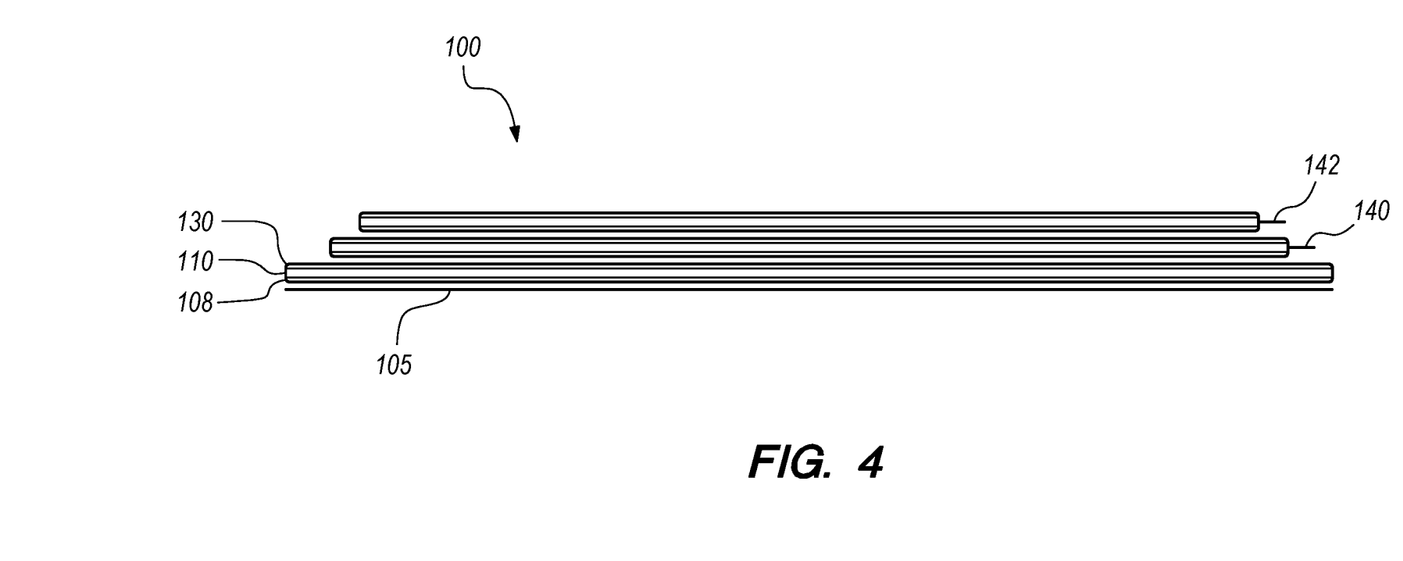
FIG. 4 is side elevation view of an absorbent pad having a plurality of individual, removeable cores.

As illustrated in FIG. 2, each tab assists the user in removing a single layer from the absorbent pad. For example, as shown in FIG. 2-4, once the top inner layer 106 has become soiled or is otherwise in need of replacement, the tab 142 may be grasped and the layer 106 may be pulled upward, separating it from the underlying layer 104. The underlying layer 104 is now exposed for use while remaining attached to the layer 102 below. In this manner, each layer may be used successively until the final layer, in this example outer layer 102, is used and finally discarded.

Figure 5:
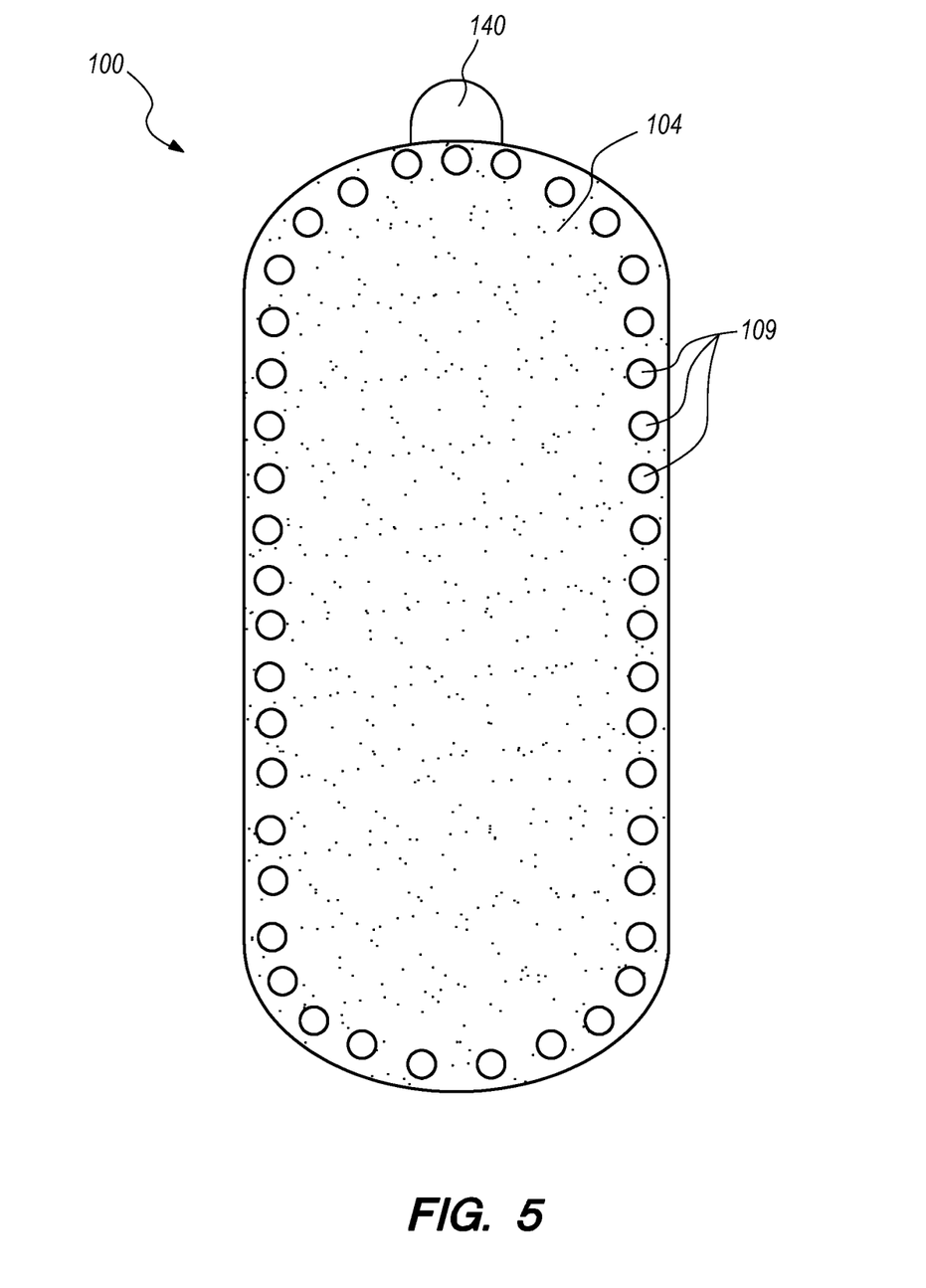
FIG. 5 is a bottom plan view of a layer having a perimeter of adhesive dots.
Figure 6:
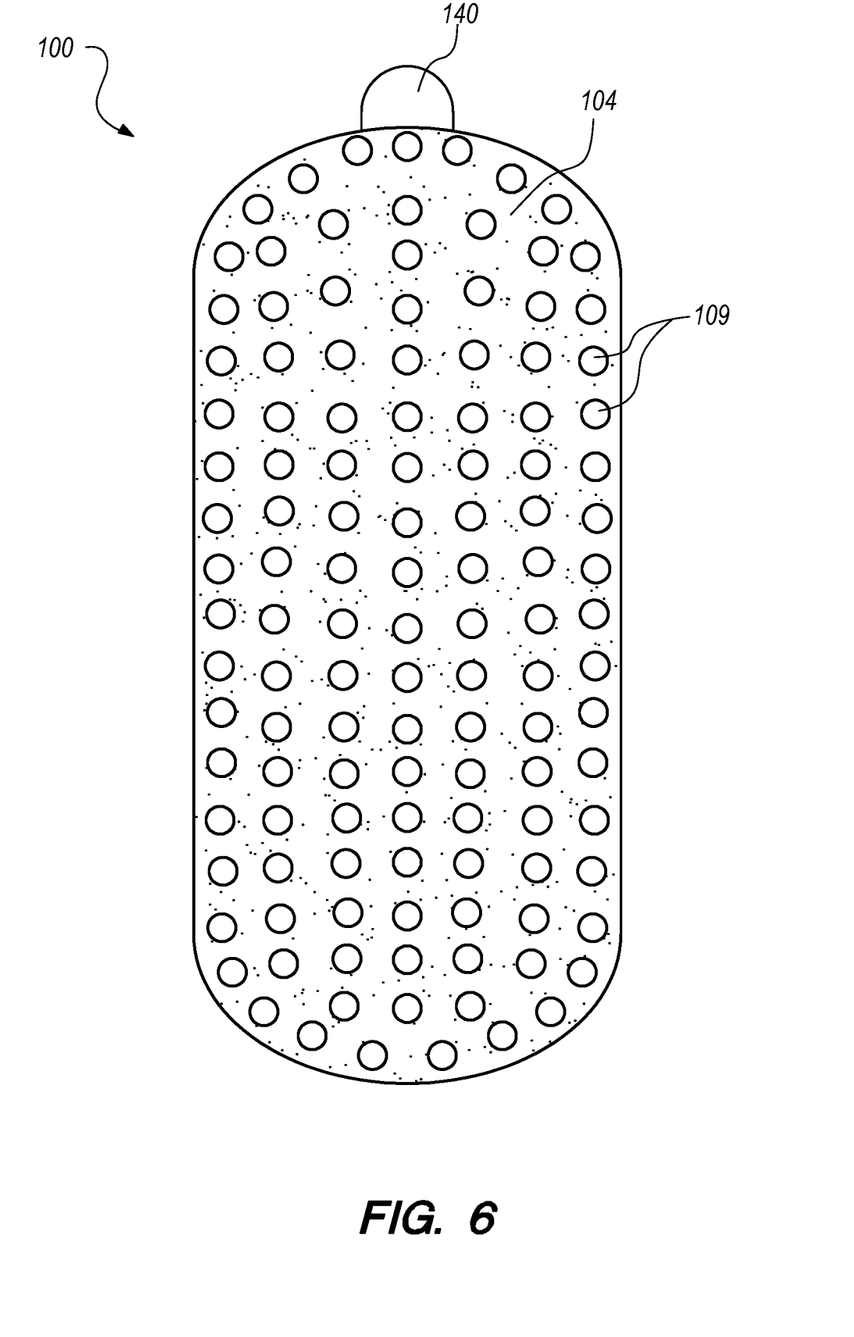
FIG. 6 is a bottom plan view of a layer having a plurality of adhesive dots coextensive with the layer.
Figure 7:
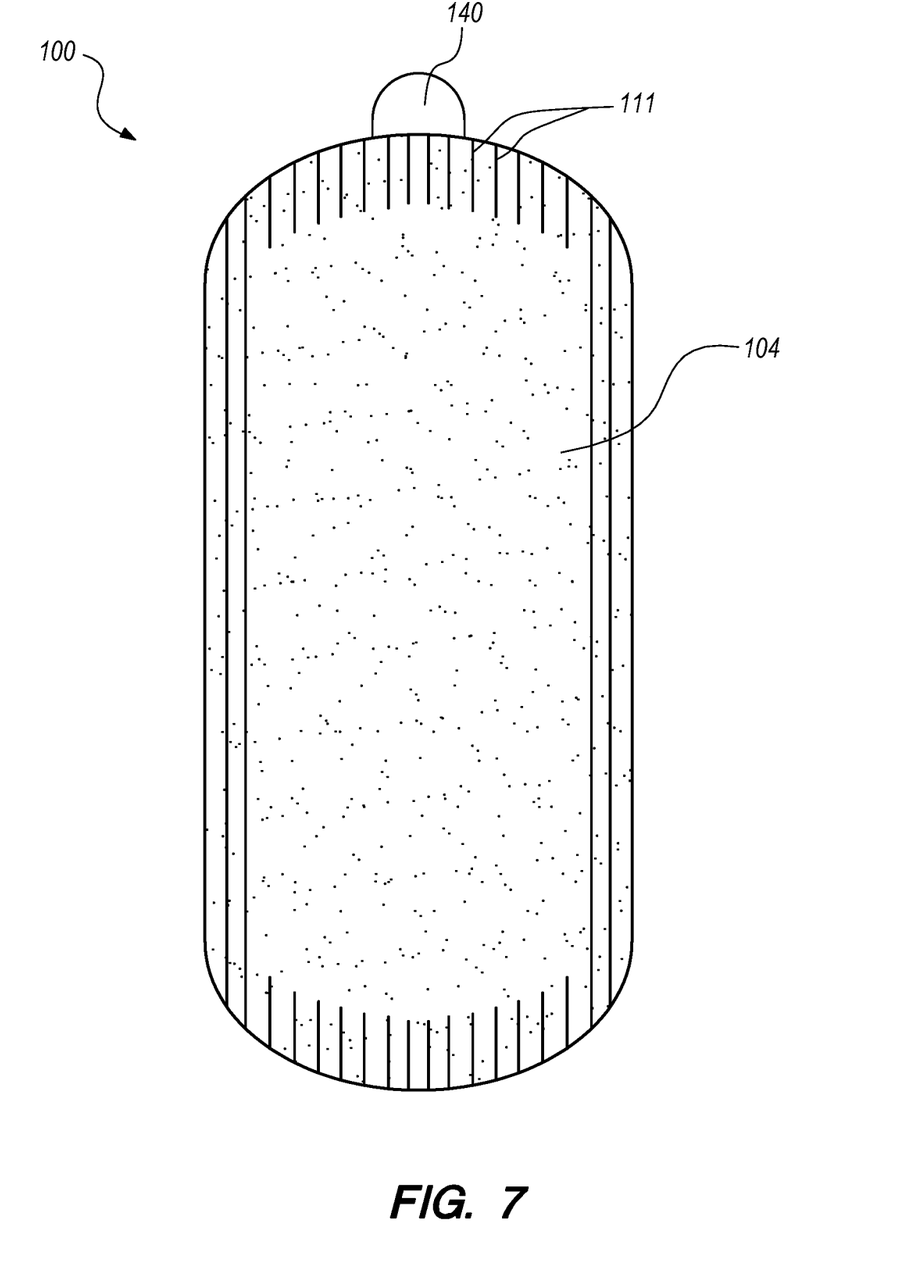
FIG. 7 is a bottom plan view of a layer having a perimeter of adhesive lines.
Figure 8:
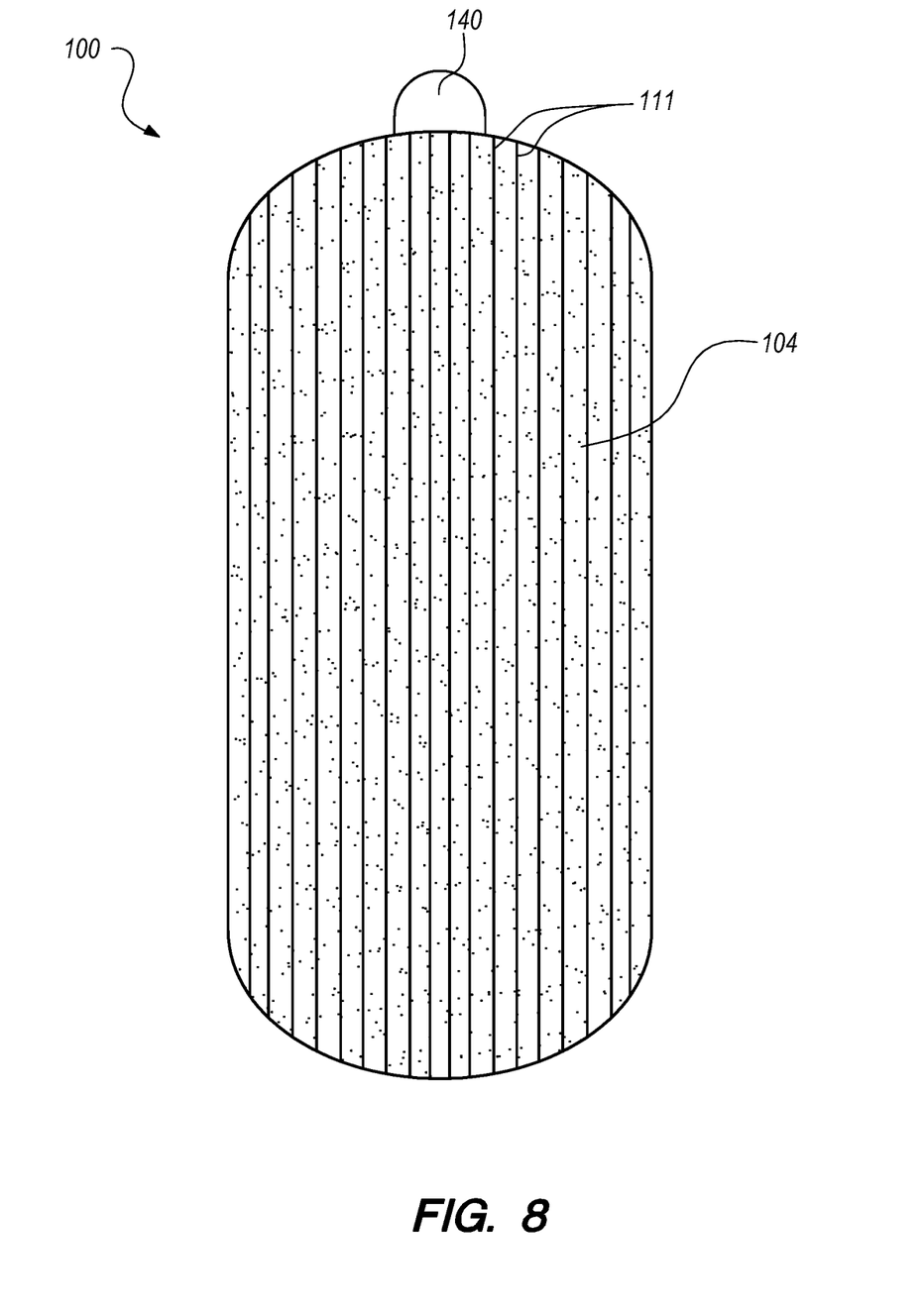
FIG. 8 is a bottom plan view of a layer having a plurality of adhesive lines coextensive with the layer.
Figure 9:
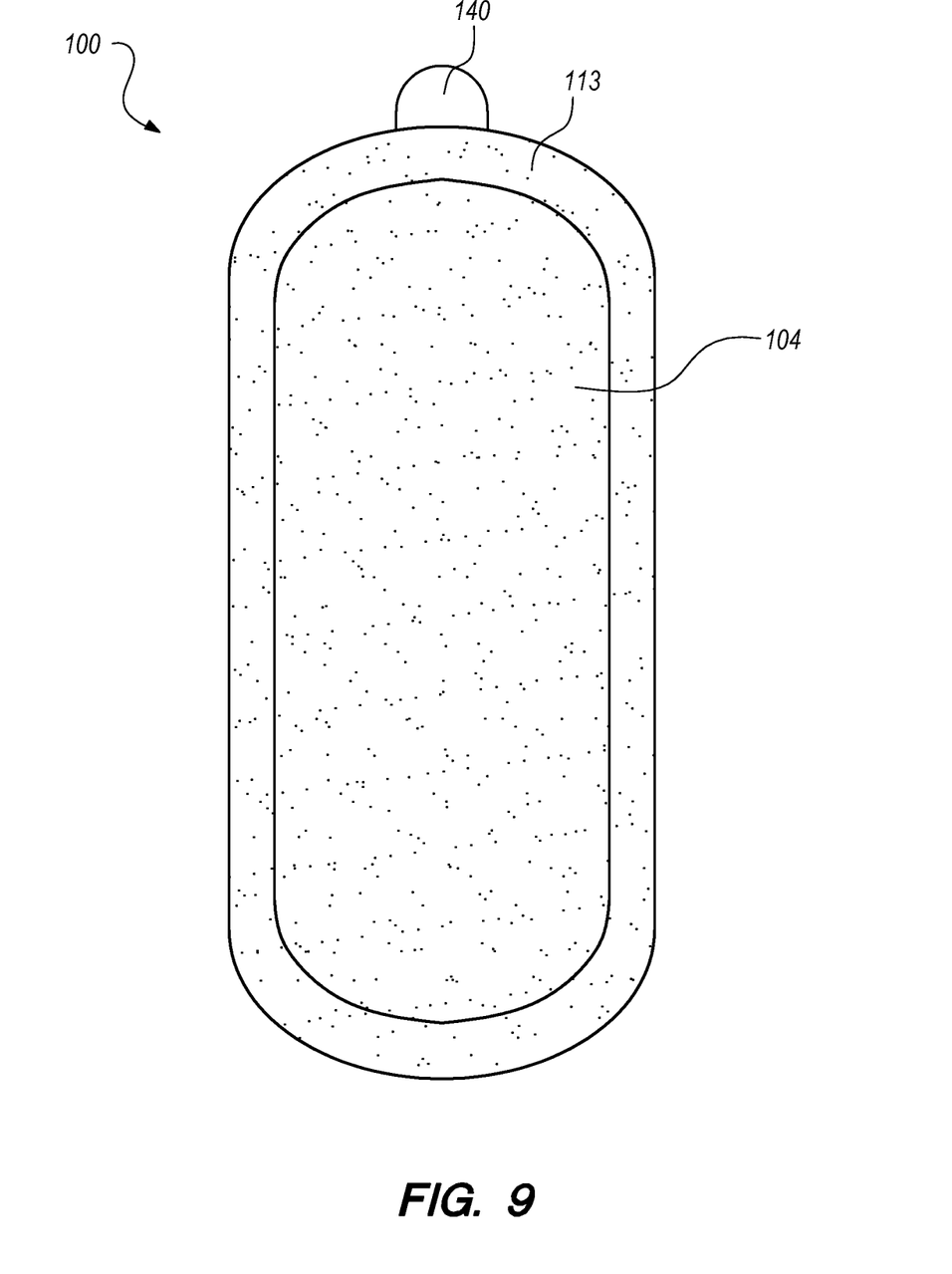
FIG. 9 is a bottom plan view of a layer having a perimeter of continuous adhesive.
Figure 10:
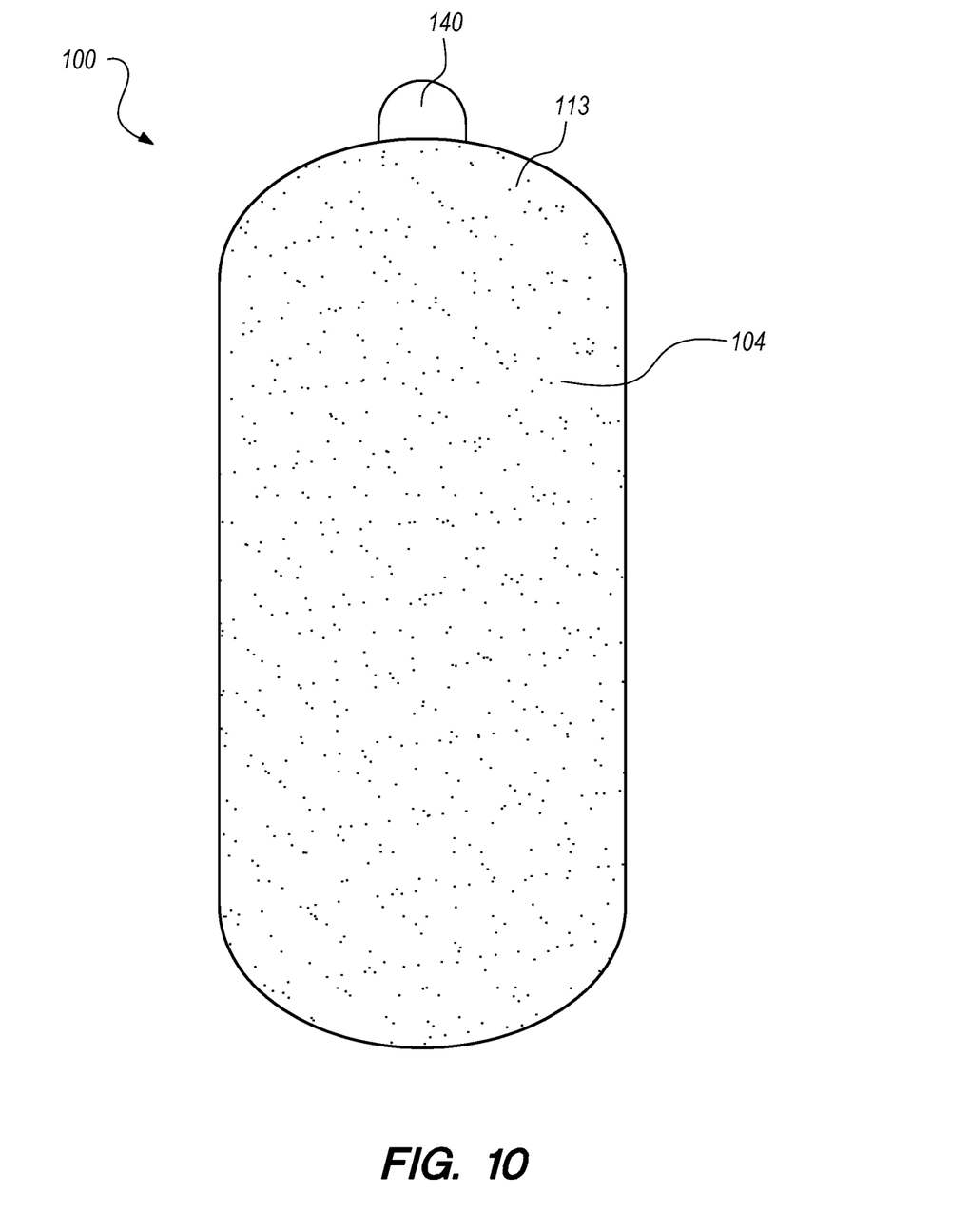
FIG. 10 is a bottom plan view of a layer having an adhesive coextensive with the layer.

The layers may be attached to one another by various means, such as an adhesive layer. For example, each layer may be adhered to the adjacent layer, such that an outside surface of layer 106 is attached to an inside surface of layer 104 and an outside surface of layer 104 is attached to an inside surface of layer 102. Such adhesion may be accomplished by the adhesive layer positioned between the layers. Such adhesive layer may be a pattern of adhesive dots 109 positioned around the perimeter of the layer (FIG. 5) or, over some portion or all of the surface of the layer (FIG. 6). For example, as illustrated in FIG. 5, a series of adhesive dots 109 may be applied to the outer surface of the inner layer 104 in a spaced apart pattern around the periphery of the layer. These adhesive dots may then attach layer 104 to the underlying layer 102. Alternatively, the adhesive layer may be a pattern of adhesive lines 111, as shown in FIGS. 7-8, positioned around the perimeter of the layer or cover some portion or all of the surface of the layer. Further, as shown in FIGS. 9-10, a continuous adhesive layer 113 may be positioned in a continuous fashion around the perimeter of the absorbent pad 100 or may cover all of the surface of the layer. In addition, the layers may be attached by ultrasonic welding, hook and loop, or other fastening means.

Further, in an alternate embodiment, the outside surface of the first layer 102 may be attached to a wearer's undergarment by various means. For example, a release liner 105 (FIG. 4) or backing may be adhered to the outside surface of the first layer 102. When a user desires to use the absorbent pad 100, the user would remove the release liner and adhere the absorbent pad to the desired location on their undergarment. It will be appreciated that having an adhesive layer on the outside surface of first layer 102 will prevent the absorbent pad from repositioning while a wearer is being active. It can also allow a wearer to remove each layer with only one hand, instead of having to hold the absorbent pad 100 with a hand while removing the soiled layer with the other. The adhesive may be applied to the outside surface of the first layer 102 in a similar fashion to the outside surface of the second and third layers 104, 106. Specifically, such adhesive may be positioned around the perimeter of the layer, in a pattern of lines or dots, over some portion or all of the outside surface of the first layer 102.

In alternative embodiments, each inner layer may be independently attached to the outer layer. For example, an outer surface of layer 104 may be attached to an inner surface of layer 102, and an outer surface of layer 106 may be attached to an inner surface of layer 102 outside a periphery of layer 104 such that layer 106 is not directly adhered to layer 104.

Referring back to FIGS. 1-3, the layers of the absorbent pad 100 may be arranged in decreasing size, such that inner layer 104 has a smaller area than outer layer 102 and innermost layer 106 has a smaller area than layer 104. Alternatively, the layers may progress from smaller to larger in the opposite directions, such that the innermost layer is larger than subsequent outer layers. In a further alternative, the size of the layers may alternate. For example, the middle layer 104 may be smaller in diameter than the outer layer 102 and inner layer 106. In this manner, the periphery of the inner layer 106 could be directly attached to the outer layer 102 as described above.

The size and shape of the absorbent pad 100 may be configured as would be appropriate for the intended use. For example, the pad may have a generally rectangular overall shape. The pad 100 may also have a narrower or wider shape than the shape indicated. The absorbent core 110 of each layer may follow the general outline of the layer's periphery, or it may diverge as appropriate. Again, the central portion 112 of the absorbent core 110 may have a generally hourglass shape that diverges from the layer's outer periphery. In addition, the end portion 114 of the absorbent core 110 may have a more rounded periphery than the overall layer. In embodiments of the absorbent pad, the layers may each have the same or similar shape, varying possibly only in size. Alternatively, the layers may have different shapes.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious various thereof is contemplated as falling within the spirit and scope of the invention, which is set forth in the following alternative embodiments.

What is claimed is:

1. An absorbent article comprising:
   a first layer comprising:
      a first periphery;
      a first liquid impervious backsheet;
      a first absorbent core positioned adjacent the backsheet and proximal the wearer; and
      a first moisture pervious topsheet;
   a second layer comprising:
      a second periphery;
      a second liquid impervious backsheet;
      a second absorbent core positioned adjacent the backsheet and proximal the wearer;
      a second moisture pervious topsheet; and
      a second-layer tab coupled to and protruding from a peripheral edge of the second layer and extending beyond the second periphery; and
   a third layer comprising:
      a third periphery;
      a third liquid impervious backsheet;
      a third absorbent core positioned adjacent the backsheet and proximal the wearer;
      a third moisture pervious topsheet; and
      a third-layer tab coupled to and protruding from a peripheral edge of the third layer;
   wherein the second layer is removably adhered to the first layer such that the second backsheet contacts the first topsheet;
   wherein the third layer is removably adhered to the second layer such that the third backsheet contacts the second topsheet;
   wherein the second periphery is positioned within and spaced apart from the first periphery for the entirety of the first periphery;
   wherein the third periphery is positioned within and spaced apart from the second periphery for the entirety of the second periphery; and
   wherein the third-layer tab is spaced a distance away from the second-layer tab.

2. The absorbent article of claim 1, wherein the second layer is removably adhered to the first layer at least in part by an adhesive positioned between the second layer and the first layer.

3. The absorbent article of claim 2, wherein the adhesive comprises a first pattern of adhesive dots positioned on the second backsheet in an area adjacent to a periphery of the second backsheet.

4. The absorbent article of claim 3, wherein the adhesive further comprises a second pattern of adhesive dots that extends over substantially all of a central area of the second backsheet.

5. The absorbent article of claim 4, wherein the second pattern differs from the first pattern.

6. The absorbent article of claim 2, wherein the adhesive extends across a peripheral area of the second backsheet and does not extend across a central area of the second backsheet.

7. The absorbent article of claim 6, wherein the adhesive comprises a pattern of spaced adhesive dots positioned uniformly and completely around a perimeter of the second backsheet.

8. The absorbent article of claim 1, wherein the second layer is removably adhered to the first layer at least in part by an ultrasonic weld.

9. The absorbent article of claim 1, wherein the second layer is removably adhered to the first layer at least in part by hook and loop.

10. The absorbent article of claim 1, wherein each absorbent core comprises a super absorbent polymer.

11. The absorbent article of claim 1, wherein the absorbent core comprises an embossed top and an embossed bottom.

12. The absorbent article of claim 1, further comprising a release liner coupled to an outside surface of the first backsheet.

13. The absorbent article of claim 12, wherein the release liner is coupled to the outside surface of the first backsheet via an adhesive in a plurality of spaced apart bonding sites.

14. The absorbent article of claim 1, wherein the second layer has a generally hour-glass shape.

15. An absorbent article comprising:
   a first layer, a second layer, and a third layer; wherein an outside surface of the third layer is coupled to an inside surface of the second layer and an outside surface of the second layer is coupled to an inside surface of the first layer;
   wherein the first layer, the second layer, and the third layer each comprise:
   an absorbent core positioned in between a liquid impervious back sheet and a moisture pervious inner layer; and
   an adhesive;
   wherein the adhesive is positioned on the outside surface of the second layer and on the outside surface of the third layer;
   wherein a second-layer tab is coupled to an edge of each of the second layer and a third-layer tab is coupled to an edge of the third layer;
   wherein the third-layer tab is spaced a distance away from the second-layer tab; and
   wherein the third layer is nested into the second layer such that a periphery of the third layer is spaced inwardly from a periphery of the second layer around the entire second layer periphery and the second layer is nested into the first layer such that the periphery of the second layer is spaced inwardly from a periphery of the first layer around the entire first layer periphery.

16. The absorbent article of claim 15 further comprising a release liner coupled to the first layer.

17. The absorbent article of claim 15, wherein the absorbent core comprises an embossed top and an embossed bottom.

18. The absorbent article of claim 15, wherein the adhesive is positioned around a perimeter of the second layer and around a perimeter of the third layer.

19. The absorbent article of claim 15, wherein the adhesive comprises a pattern of adhesive dots positioned uniformly and completely around a perimeter of the second layer and around a perimeter of the third layer.

20. The absorbent article of claim 15, wherein the absorbent article is a disposable incontinence pad.

* * * * *